United States Patent
De Godzinsky

(10) Patent No.: US 7,212,611 B2
(45) Date of Patent: May 1, 2007

(54) METHOD AND APPARATUS FOR LIMITING A RAY BEAM

(75) Inventor: Christian De Godzinsky, Vanda (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 10/478,970

(22) PCT Filed: May 29, 2002

(86) PCT No.: PCT/FI02/00461

§ 371 (c)(1),
(2), (4) Date: Jul. 19, 2004

(87) PCT Pub. No.: WO02/097827

PCT Pub. Date: Dec. 5, 2002

(65) Prior Publication Data

US 2004/0234034 A1 Nov. 25, 2004

(30) Foreign Application Priority Data

May 29, 2001 (FI) .................................. 20011119

(51) Int. Cl.
*G21K 1/04* (2006.01)
(52) U.S. Cl. ...................... 378/150; 378/151; 378/152
(58) Field of Classification Search ................ 378/147, 378/150–153, 38–40; 250/503.1, 505.1
See application file for complete search history.

(56) References Cited

U.S. PATENT DOCUMENTS

| 4,794,629 A | * | 12/1988 | Pastyr et al. ................. 378/152 |
| 4,916,723 A | | 4/1990 | Geluk |
| 5,086,444 A | * | 2/1992 | Bartmann ................... 378/152 |
| 5,136,627 A | | 8/1992 | Conrads et al. |
| 5,237,599 A | * | 8/1993 | Gunji et al. ................. 378/148 |
| 5,396,533 A | * | 3/1995 | Holzermer .................. 378/150 |

FOREIGN PATENT DOCUMENTS

| DE | 32 36 082 A1 | * | 3/1984 |
| DE | 297 10 724 U1 | * | 9/1997 |
| FI | 894310 | | 3/1990 |
| GB | 2 291 326 | | 1/1996 |

* cited by examiner

*Primary Examiner*—Edward J. Glick
*Assistant Examiner*—Jurie Yun
(74) *Attorney, Agent, or Firm*—Wolf Block Schorr & Solis-Cohen LLP

(57) ABSTRACT

The invention concerns a method and apparatus for limiting a ray beam, especially in connection with an x-ray imaging equipment. The invention comprises a collimator construction in which a primary blade element (4) is moved directly by means of an actuator (3) and where at least one secondary element (5, 20) is movable in connection with the primary element (4), but does not move dependent on the movements of it when the distance between the said elements (4, 5, 20) is within at least one certain operating range concerning them.

28 Claims, 2 Drawing Sheets

--PRIOR ART--

METHOD AND APPARATUS FOR LIMITING A RAY BEAM

FIELD OF THE INVENTION

The present invention relates to a method as defined in the preamble of claim 1 and to an appratus as defined in the preamble of claim 13 for limiting a ray beam, in particular in connection with x-ray imaging equipment.

BACKGROUND OF THE INVENTION

The invention is applicable for use e.g. in mammography and especially in dental radiography, in which it is possible to distinguish e.g. so-called intraoral imaging, which typically means imaging individual or a few teeth, so-called panoramic imaging, which means producing a layer image, i.e. a tomogram of the dental arch, and so-called cephalometric imaging, which typically means producing a transillumination image of the entire skull area. Often the same dental imaging apparatus is used for taking both panoramic and cephalometric images, and today increasingly also for producing various special images of different parts of the dental arch.

In dental panoramic imaging and cephalometric imaging of the skull area as mentioned above, for example, it is necessary to provide for different purposes apertures of various shapes and sizes between the radiation source and the film or equivalent, in order to be able limit the x-ray beam to apply it to the object to be radiographed according to the imaging requirements in each case. For producing different ray beams, solutions are known whereby the beam is limited by means of various blades, i.e. collimators. Typically, one or more blades having a number of different apertures or shapes for forming different apertures are used. Generally, one aperture is used at a tine, and when the imaging apparatus is to be used in a different mode, the ray beam is limited correspondingly by using a different aperture. However, this type of arrangements have the drawback that the user can only apply those forms of ray beam that are provided in the blades. On the other hand, the space available in the imaging apparatus imposes certain restrictions as to the number of different blades, and the arrangements needed to allow replacement of blades also involves certain problems regarding the convenience of use of the apparatus and the need to store the blades.

Another prior-art solution is to use e.g. a so-called four-blade-type collimator for limiting the ray beam. In such a collimator solution, each one of the four blades is driven by a separate actuator, so this type of solutions are implemented using e.g. four different actuators to move two of the blade vertically and two horizontally, thus allowing a desired aperture size to be provided for the ray beam. A drawback with this type of solutions is the large number of actuators, which also leads to complex electronics for the control of the actuators. Moreover, having a large number of actuators increases the cost of the construction. A further problem is that a relatively large space is needed for the actuators.

A prior-art blade mechanism is disclosed in Finnish patent application no. 894310, corresponding Japanese utility model no. 63-119939. This mechanism comprises two blade elements, which are provided with holes of different sizes and can be driven individually relative to each other in the horizontal direction. The limiting of the ray beam is controlled via interlaced disposition of the holes, and one of the blade elements is provided with a wedge-shaped soft tissue filter for use in certain imaging modes. One of the drawbacks of this solution is that, though the ray beam can be limited in a stepless manner in the horizontal direction, stepless limiting is not possible in the vertical direction since limiting of the beam is implemented using apertures that are provided with notches to allow an appropriate aperture height to be achieved. This solution thus provides only a certain preselected number of aperture heights. A further drawback is an expensive and complicated structure.

OBJECTS AND SUMMARY OF THE INVENTION

The object of this invention is to eliminate some of the above-mentioned drawbacks and to achieve a reliable method and a corresponding apparatus with reasonable cost for limiting the ray beam, especially in an x-ray imaging apparatus. The method of the invention is characterized by what is presented in the characterizing part of claim 1, and the apparatus of the invention is characterized by what is presented in the characterizing part of claim 13. A few other embodiments advantageous to the invention are presented in the other claims.

The solution according to the invention provides the advantage of making it possible to implement a countless number of apertures of different shapes and sizes at a reasonable price using the same collimator equipment. The minimum number of actuators needed is only one actuator e.g. for horizontal motion and one actuator for each additional direction of motion, such as vertical motion. Moreover, due to the small number of actuators, the space requirement of the construction is small. As an additional advantage afforded by the small number of components, a mechanical solution for limiting the ray beam in an x-ray imaging apparatus or other medical imaging apparatus or a corresponding apparatus is achieved that is reliable in use, as maintenance-free as possible and of low cost.

BRIEF DESCRIPTION OF THE DRAWINGS

In the following, the invention will be described in detail with the aid of an example related to radiography, with reference to the attached drawings. In the drawings.

DETAILED DESCRIPTION OF THE INVENTION

Figure 1:
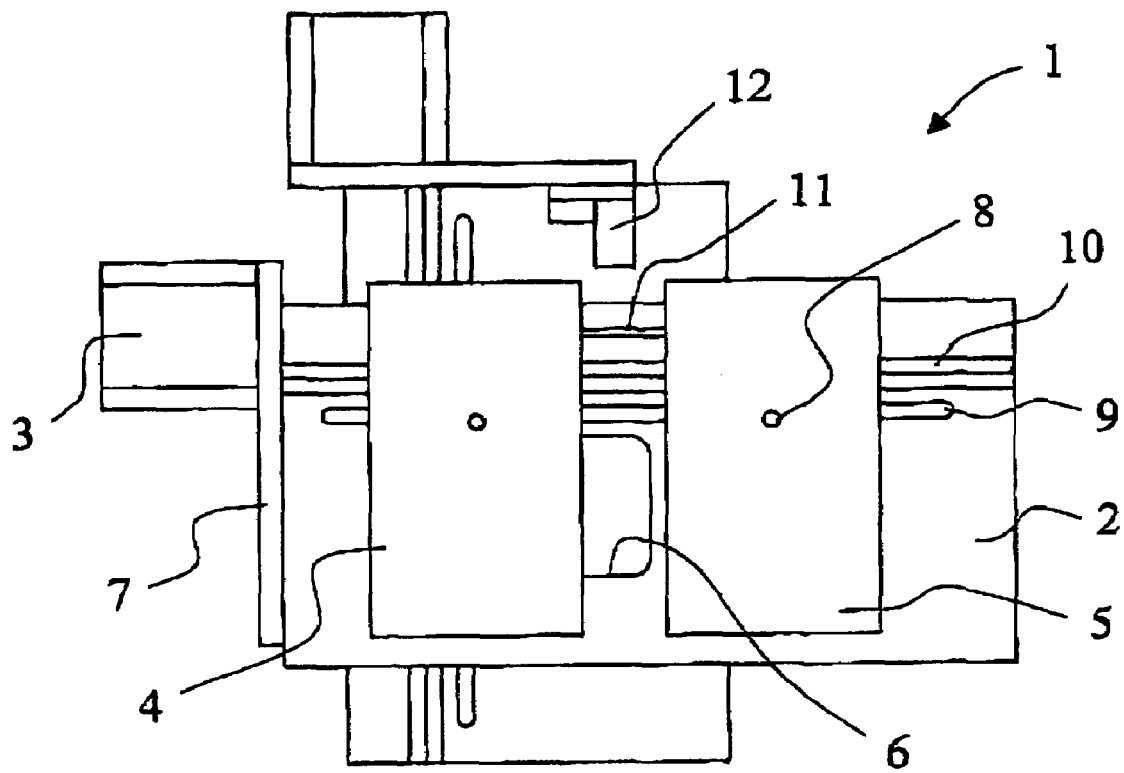
FIG. 1 presents a simplified front view of the solution of the invention.
Figure 2:
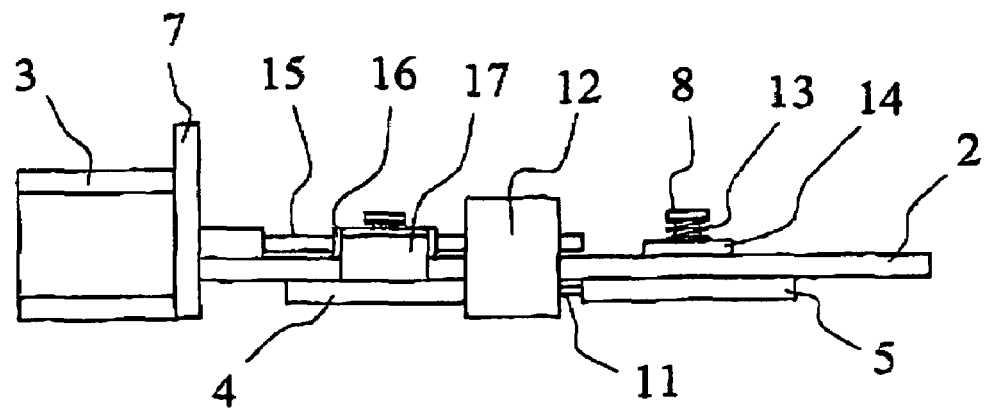
FIG. 2 presents a top view of the solution presented in FIG. 1, with the vertically movable blade mechanism removed.

The apparatus according to the invention will be described first to make it easier to understand the method for limiting the ray beam. FIGS. 1 and 2 present a blade mechanism 1 according to the invention in a simplified form, which comprises a horizontal base plate 2 consisting of e.g. a rectangular metal plate of even thickness, which in a normal service position is placed in a substantially vertical plane with one of its longitudinal edges pointing downwards. The front surface of the base plate 2, in FIG. 1 the surface facing towards the viewer, as well as the back surface are planar surfaces substantially parallel to each other. Placed in the upper part of the front surface is a substantially horizontal guide arrangement 10 for guiding the movements of the blade elements 4, 5 of the collimator mechanism. Located below the guide arrangement 10 is an elongated guide slot 9 parallel to the guide arrangement and extending in its entire length through the base plate 2 in the thicknesswise direction of it. Further, the base plate 2 comprises a substantially rectangular radiation aperture 6 placed below the guide slot 9 to allow the passage of X-rays or equivalent. The size of the radiation aperture 6 is so chosen that it covers the required maximum dimensions in both horizontal and vertical directions.

Mounted on the front surface of the base plate 2 is a primary element 4 of the blade construction 1 and one or more secondary elements 5 so that the blade elements 4, 5 are movable substantially in the longitudinal direction of the base plate 2. In the context of this invention, primary element 4 refers to a blade element that can be moved by an actuator 3 independently of the other blade elements. Correspondingly, blade elements that are moved in direct or indirect coupling with the movements of the primary element 4 are called secondary elements 5. In the solution illustrated in FIG. 2, each blade element 4, 5 is fitted to the elongated guide slot 9 via a friction plate 14, a spring 13 and a spring stopper 8. The spring-loaded friction plate 14 can also be called a slide piece because the friction plate 14 slides along the back surface of the base plate 2 as the blade element 4, 5 is moving, thus constraining the motion of the element and ensuring that there is no play in the transverse motion.

Attached to one end of the base plate 2 is a supporting plate 7 so that the plane of the supporting plate 7 is perpendicular to the plane of the base plate 2. Mounted on the supporting plate 7 is a stepping motor 3 serving as an actuator, whose drive shaft consists of a screw 15 passing through the supporting plate 7 to the back side of the base plate 2 in a direction parallel to the plane of the base plate 2. The stepping motor 3 has been fitted to move the primary element 4 back and forth by means of the screw 15. As the screw 15 is turning, it produces a motion of a transfer element 16 provided with an internal thread and with a mechanism to which a transfer block 17 placed behind the primary element 4 is so fitted that, when the transfer element 16 is moving back and forth in the longitudinal direction of the base plate 2, the primary element 4 also moves back and forth on the front surface of the base plate 2.

Figure 3:
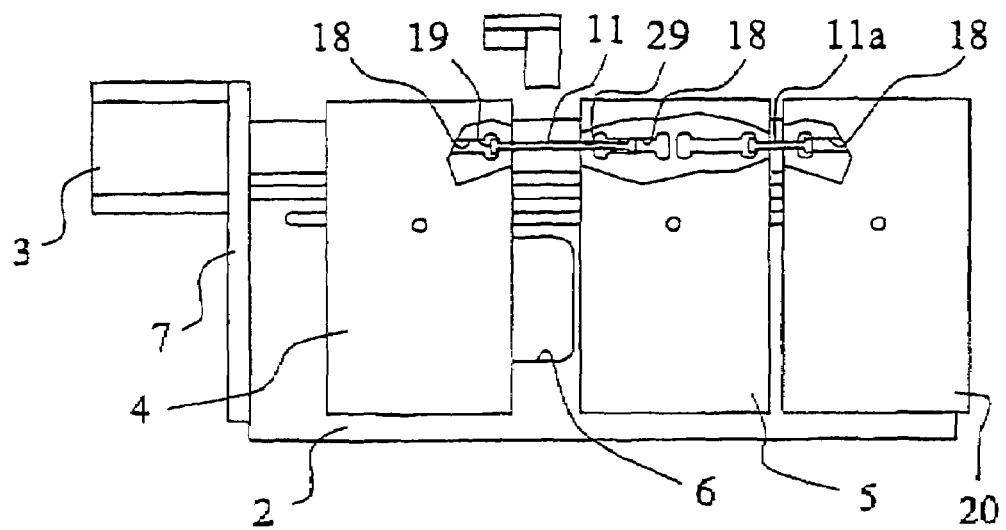
FIG. 3 presents an embodiment of a solution according to the invention in front view and partially sectioned.

The secondary element 5 of the blade mechanism 1 is coupled to the primary element 4 by means of a coupler 11 functioning as a synchronizing device, which is shown in more detail in FIG. 3. The coupler 11 is a thin round metal bar or equivalent, each end of which is provided with a gripper part 19 having a diameter larger than that of the middle part. The back race of each element 4, 5, 20 is provided with two parallel slot-like grooves 18 of a depth that is smaller than the thickness of the element in the area in question, so the grooves 18 do not extend through the element. The width of the grooves 18 has been fitted to be suitably larger than the diameter of the gripper parts 19 of the couplers 11, so the gripper 19 can move in the groove 18. At that end of each groove 18 which lies closer to the edge of the element 4, 5, 20, there is additionally a narrower groove 29 extending from the end of groove 18 to the edge of the element 4, 5, 20. The width of this groove 29 has been fitted to be suitably larger than the diameter of the middle parts of the couplers 11, so that the middle part of the coupler 11 can move in this groove. The elements 4, 5, 20 are coupled to each other by the couplers 11, 11a so that the gripping parts 19 of each coupler connect to the adjacent elements 4, 5, 20. The lengths of the couplers 11, the lengths of the grooves 18 and the extreme positions of the couplers 11 permitted by the grooves 18 have been so adjusted with respect to each other that, within a given range of the distances between two elements 4, 5, 20, the motion of one element will not change the position of the other element, but when this distance equals a limit value of such a range, the elements will move in synchronism in at least one direction of movement. By suitably selecting the various dimensions of these components of the blade mechanism 1, an arrangement is achieved in which the blade elements 4, 5, 20 can be positioned at the desired position in the blade structure.

FIG. 1 also shows a vertical base plate, which in principle comprises the same functions as the horizontal base plate 2. The vertical base plate is placed in a substantially upright position in its longitudinal direction, and so it is perpendicular to base plate 2. By means of blade elements provided on the vertical base plate, it is possible to adjust the height dimension of the ray beam.

As is evident from what was said above, the blade mechanism may comprise e.g. two secondary elements 5, 20 in addition to the primary element 4, as illustrated in FIG. 3. In a blade mechanisms comprising several secondary elements 5, 20 etc., it is possible to provide apertures of different limit dimensions by using e.g. synchronizing devices 11 of different lengths, and it is also possible to use a fixed synchronizing device 11 between two elements 4, 5, 20 etc. to produce a fixed-size aperture. It is also possible to use e.g. secondary elements 5, 20 etc. as a support for various accessories. These include e.g. a soft tissue filter used in cephalometric imaging, various additional filtering elements and blades with various fixed-shape apertures. In some embodiments, using the blade mechanism 1 of the invention makes it unnecessary to provide a separate positioning device for an accessory, which otherwise would be needed in the imaging apparatus. It is even feasible to provide an existing blade mechanism with such an accessory either by placing it on an existing blade element or by adding it to a new secondary element to be added to the mechanism. The accessory should be so designed that the area it will cover extends to a desired area or point over the radiation aperture 6.

As indicated above, the blade mechanism of the invention can be implemented in a form comprising several secondary elements 5, 20 etc. Secondary element 20 in FIG. 3 has a structure identical to that of elements 4 and 5, and it is mounted on the front surface of the base plate 2 in the same way as elements 4 and 5. This second secondary element 20 is moved on the same principle as in the case of the first secondary element 5 by coupling it to the first secondary element 5 by means of a second coupler 11a, which is otherwise identical to the first coupler 11 between the primary element 4 and the first secondary element 5 except that it is shorter. The length of the second coupler 11a that couples secondary elements 5, 20 together is naturally chosen by taking into account the desired application of the second secondary element 20. It is thus possible to connect to the front surface of the base plate 2 several secondary elements 5, 20 or other components that can be moved by moving the primary element 4.

The apparatus presented in the drawings additionally comprises a position detector 12 functioning as a reference detector. By using operating sequences fed into the control system of the apparatus and determining the position of one of the blade elements 4, 5, 20 etc. e.g. on the basis of a detection impediment (not shown in the drawings) associated with the element, the use of the entire blade system can be controlled, the dimensions of its various components being known.

Thus, according to the invention, the x-ray beam obtained from the x-ray source can be limited by moving the primary element 4 of the blade mechanism 1 and, directly or indirectly by means of it, one or more secondary elements 5, 20 etc. of the blade mechanism. An example of how to limit the ray beam for a given purpose is as follows. First, if necessary, the position of e.g. one of the secondary elements 5, 20 etc. may be detected, or for instance the primary element 4, and possibly inherently some or all of the secondary elements 5, 20 etc., too, is brought into a desired position by running an initial operating sequence defined in the operating system of the apparatus. After this, the primary element 4 is then moved by means of an actuator 3 in a direction away from the secondary element 5, 20 etc. in question so that, after a short delay at least, the secondary element 5, 20 etc. will start moving in direction of the primary element 4 as it is drawn by the primary element 4 and the associated synchronizing device 11—and possibly by other blade elements 5, 20 etc. and synchronizing devices 11, 11a etc. provided in the blade mechanism 1 between the primary element 4 and the secondary element 20 etc. in question. More specifically and referring to the attached drawings, this is done as follows. The transfer element 16 is moved by means of the rotating screw 15 of the operating shaft of the actuator 3 towards the actuator 3, and at the same time the primary element 4 connected to the transfer element 16 moves in a direction away from the secondary elements 5, 20, in this embodiment towards the actuator 3. At a certain point, after the clearance between the gripping part 19 of the coupler 11 and the groove 18 in the primary element 4 has been closed, the primary element 4 starts pulling the coupler 11 along with it. Once the primary element 4 has moved far enough so that the distance between the ends of the grooves 18 in elements 4 and 5 corresponds to the distance between the gripping parts 19 of the coupler 11, the secondary gripping part 19 of the coupler engages the edge of the groove 18 in secondary element 5 and the secondary element 5 begins to follow the primary element 4. By continuing the motion of the primary element 4 far enough in the same direction, a corresponding coupling will eventually occur in the case of the second secondary element 20, or in case of several secondary elements, for all of them as well. In the present context, that range of distances between the primary element 4 and a secondary element 5, 20 etc. within which the secondary element 5, 20 etc. remains stationary regardless of the primary element 4 being moved is called an operating range of by the elements in question. Thus, concerning the current example and a construction including only one secondary element 5, when moving of the primary element 4 in the direction away from the secondary element 5 is continued the elements 4, 5 move in synchronism at a distance from each other consistent with a maximum limit value of an operating range between them, until the secondary element 5 (or a corresponding additional secondary element 20 when two secondary elements 5, 20 are used for limiting the beam) has been brought to a desired point past that edge of the aperture to be formed between the elements 4, 5 which lies on the side to the secondary element 5. After this, the direction of motion of the primary element 4 is changed and it is driven towards the secondary element 5 until a minimum limit value of the aforesaid operating range between them is reached—this value being zero in this particular example, i.e. until the primary element 4 and the first secondary element 5 meet. So far, the secondary element 5 has remained stationary, but as the movement is continued, the primary element 4 will start pushing the secondary element 5 in front of it and it will go on pushing it until the secondary element 5 has reached the desired position to form the first edge of the aperture being formed between the elements 4, 5, i.e. the edge on the side of the secondary element 5. (It is again naturally possible to drive the primary element 4 in an appropriately corresponding manner in case the aperture is to be created between two secondary elements 5, 20). After this, the direction of motion of the primary element 4 is changed again and the primary element 4 is driven (and in case of using two secondary elements, also the secondary element 5 adjacent to the said additional secondary element 20 is pulled) to the desired position within the operating range so that the second edge of the aperture being formed will be created, while the said secondary element 5, 20 forming the said first edge of the aperture remains stationary.

Alternatively, in the above-described embodiment, the second edge of the aperture can be established by driving the primary element 4, or the secondary element 5, 20 etc. forming it, past the point of the second edge of the aperture being formed by a given distance, changing the direction of movement and driving the element 4, 5 in question to the desired position to form the second edge of the aperture. This short back-and-forth motion at the final stage of the process of limiting the aperture makes it possible to eliminate any inaccuracies in positioning of the element in question that might otherwise result from mechanical clearances.

In another possible embodiment of the invention, after the above-described possible preliminary position-identifying and/or initial-element-positioning operations have been performed, the primary element 4 is driven by means of the actuator 3 in the direction of a given secondary element 5, 20 etc. until, at the latest after a short delay, i.e. after a minimum limit value of an operating range pertaining to the elements concerned is reached (which in a particular case where the limit value is zero, i.e. where the secondary element in question is the secondary element 5 adjacent to the primary element 4, corresponding a situation where the primary element 4 and the secondary element 5 in question meet) the movement is continued in the same direction, thus causing the secondary element 5, 20 etc. to move in the direction in question at a distance from the priority element 4 corresponding to the minimum limit value of the said operating range between the elements concerned, until the secondary element 5 has reached the desired position to form a first edge of an aperture being formed between the secondary element 5, 20 etc. in question and the primary element 4 (or between the secondary element 20 etc. in question and the secondary element 5, 20 etc. adjacent to it in direction of the primary element 4). After this, the direction of movement is changed and the primary element 4 is driven within the aforesaid operating range, while the secondary element 5, 20 etc. in question remains stationary, so that the primary element 4, or the aforesaid secondary element 5, 20 etc. adjacent to the secondary element 5, 20 etc. in question, moves to its desired position to form the second edge of the aperture. In connection with this procedure, too, it is possible to perform a back-and-forth movement of the primary element 4 at the final stage, as described concerning the embodiment described above.

The collimator structure of the invention may comprise a structure where secondary elements 5, 20 etc. are provided on either or both sides of the primary element. The above-described methods of moving the elements are naturally applicable for use in this type of embodiments as well.

As described above, in the embodiment according to the attached drawings the secondary elements 5, 20 are moved either by means of a synchronizing device 11, 11a or by means of the primary element 4 or, via it, by another secondary element 5, depending on the details of the collimator construction and direction of motion.

The height dimension of the ray beam can be limited as described above by means of a second blade mechanism, which in the embodiment illustrated in FIG. 1 is mounted in a perpendicular position relative to the above-described mechanism 1, e.g. immediately behind it.

If the blade mechanism 1 comprises several secondary elements 5, 20 etc., these can all be moved on the above-described principle exactly to the desired position by means of the couplers 11, 11a, etc. serving as synchronizing devices. The couplers 11, 11a may be of different lengths relative to each other in order to have the maximum aperture sizes achievable by different blade element pairs different. As described above, using operating sequences provided in the control system of the apparatus, by identifying the position of at least one blade element and knowing the widths of the elements 4, 5, 20 etc., the positions and lengths of the grooves 18 as well as the lengths of the couplers 11, 11a etc., it will be possible to bring any one of the blade elements into a desired position in a controlled manner.

The present invention also makes it possible to use the blade mechanism so as to implement in a simple manner the scanning of an object to be radiographed by a ray beam. For example in the solutions presented in the attached drawings, the length of each synchronizing device 11, 11a corresponds to a given maximum distance between two elements 4, 5, 20 etc., and when this length is chosen to allow the formation of a ray beam of a desired size at its maximum, the scanning can be implemented by driving the primary element 4 in the opposite direction relative to a secondary element 5, 20 etc., with the secondary element 5, 20 etc. thus following the primary element 4 at the desired maximum distance allowed by the synchronizing device 11, 11a etc. which connects the secondary element 5, 20 etc. in question to the primary element 4—or to a secondary element 5, 20 etc. adjacent to it in the direction of the primary element 4. If necessary, prior to such an imaging scan, the primary element 4 has first been moved in the direction of the secondary element 5, 20 etc. in question past its position at which the scanning is to be started at least such a distance that after being subsequently moved in the opposite direction to its scanning starting position, the aperture between those blade elements to be used for scanning will be at its maximum. This kind of a solution can be used e.g. in digital dental cephalometric imaging, where scanning of the beam according to the invention can be implemented by moving the blade elements only as opposed to moving the entire x-ray tube head together with the blade mechanism.

The invention thus offers, in a solution comprising two or more secondary elements 5, 20 etc., the possibility to provide even between certain secondary elements 5, 20 etc. a synchronizing device 11a etc. permitting a certain maximum distance between the elements and to use an aperture according to such a distance for implementing the scanning movement of the ray beam. In such said solutions comprising several secondary elements it is further possible to use several synchronizing devices 11a etc. of different lengths intended for different applications.

As for the synchronizing device 11, 11a, or more generally the motion transmission mechanism between the elements, let it be further stated that, although the blade elements 4, 5, 20 etc. in the above-described embodiments are directly in contact with each other in their mutual minimum distance positions, the arrangement can also be implemented so that the minimum distance between adjacent elements corresponds e.g. to a ray beam of a desired width. In this case, for example, the above-described imaging scan can be implemented by pushing the first element associated with an appropriately designed synchronizing device in question from the direction of the second of these elements. Another feasible principle of implementing the transmission mechanism is to provide, in addition to the minimum and maximum distances possible between the adjacent elements allowed by the mechanism, at least one fixed mutual distance between adjacent elements. Such a transmission mechanism can be e.g. a synchronizing device provided with means, such as e.g. solenoids, for locking it to a desired position in relation to a blade element. This kind of constructions thus include more than one operation range between element pairs and allow for scanning with beams of different sizes by using a smaller amount of synchronizing devices and secondary elements. Further, if such said means for locking the synchronizing device are arranged in connection with both of the elements associated with it, it will be possible to implement the scanning movement using a ray beam corresponding to this locked position in both directions.

Figure 4:
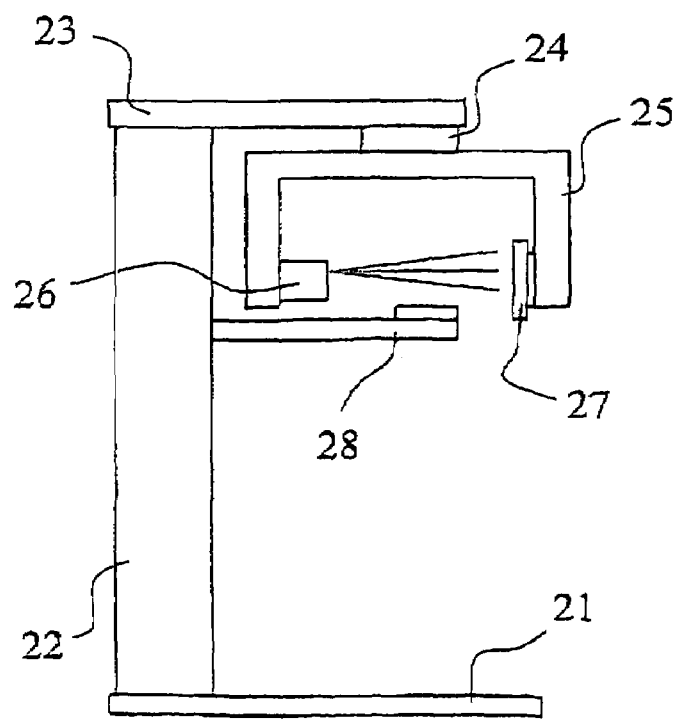
FIG. 4 presents a typical panoramic x-ray imaging apparatus in a simplified side view.

FIG. 4 presents a typical panoramic x-ray apparatus. The apparatus has a base 21 and a column-like body 22 mounted on it, with a cantilever-type supporting element 23 pivotally mounted on the upper end of the body so as to be rotatable with respect to the body 22, for supporting the radiography equipment. Similarly pivotally mounted at the outer end of the supporting element 23 is a projecting intermediate supporting element 24. Rotatably mounted at the outer end of the intermediate supporting element is an imaging arm 25, which supports a panoramic film cassette 27 and an X-ray source 26, and which is often called C-arm with reference to its shape. The blade equipment of the invention is placed on the imaging arm at a position near the x-ray source 26, between the x-ray source and the panoramic film cassette. In addition, attached to the column-like body 22 is a positioning support 28 to help position the person to be radiographed. Instead of being mounted on a column-like body, the cantilever-type supporting element 23 at the upper end may also be pivotally mounted on a wall structure, and the other actuators mentioned here may likewise have a different structure and function. The structure illustrated in FIG. 4 has been simplified by removing parts from it that are inessential in respect of the invention.

An apparatus as presented in FIG. 4 can also be used for cephalometric by integrating a cephalometric imaging station 30 with a panoramic x-ray radiography apparatus. The cephalometric imaging station comprises means for holding a film cassette 31 or equivalent and a patient support 32 for the object to be radiographed. Cephalometric imaging is carried out by positioning the depicting means so that the x-ray beam emitted by the radiation source 26 can be directed towards the object to be radiographed and the film cassette 31, and by limiting the x-ray beam in accordance with the requirements of each imaging mode.

Thus, by using the solution of the invention, the ray beam can be limited accurately in accordance with the requirements of typical panoramic imaging as well as cephalometric imaging and eventual other special imaging requirements so as to apply it to an area of exactly the desired form and size, e.g. to the area of mandible teeth only. The film may naturally be replaced with an electric medium for receive imaging information, e.g. with a narrow detector for implementing scanning panoramic or cephalometric imaging.

It is obvious to a person skilled in the art that the invention is not limited to the examples described above, but that it may be varied within the scope of the claims presented below. Thus, for example, the structure of the apparatus may differ from that described above in that, instead of stepping motors, the actuator 3 may consist of some other device suited for the purpose. Similarly, instead of pin-like couplers serving as synchronizing devices, it is possible to use thread-like, chain-like or ring-like couplers. Moreover, movements of the secondary elements may also be realized without any such synchronizing devices between the blade elements as described in reference to the attach drawings by using a properly formed primary element or some other means directly movable by the actuator, i.e. e.g. where the primary construction would either move the secondary element into the direction of its movement or leave it in place in dependence on the direction of its movement and its location in relation to the secondary element. As an example of such an embodiment the blade construction may consist of a U-shaped primary element, i.e. a one-piece element having two blades at a distance from one another, and at least one secondary element arranged between those blades having a smaller width than the said distance between the blades of the primary element. By arranging the dimensions of the construction properly also this kind of solutions can be used for scanning, and it is obviously possible to provide this kind of mechanisms with synchronizing devices as described above, too.

Further, the number of blade elements, both in the vertical plane and in the horizontal plane, may vary within a desired range. Similarly, when beams of different shapes are to be created, a number of blade element pairs or series can be used and moved diagonally relative to each other, which makes it possible to implement e.g. circular or nearly circular apertures of different sizes and at any position within the maximum dimensions of radiation aperture of the construction.

The operating sequences used in the invention may also be implemented in other ways in addition to those described above. Further, the primary element may be placed at some other position in the set of blade elements than at the outmost position as assumed in the attached figures. On the other hand, the position of any or even every one or the elements in the blade structure can be detected. In addition, the above-mentioned position detector may be e.g. an absolute detector that knows the position of at least one blade element all the time. In this case, it will not be necessary to separately establish the position of a given element at the beginning of an operating sequence. The detection of the position of a blade element may also be implemented in some other known way, or it may even be totally omitted in case an appropriate operating sequence that drives at least one of the elements into a known initial position in its operation range is used.

It is also possible to apply the invention in mammography, where for example, a ray beam of conventional size is first used to image the entire breast, and if a lesion is detected, the depicting means are then moved into a magnifying imaging position during the same imaging operation, and the ray beam limited using means provided by the invention so that the beam will only cover the area of the lesion.

Yet another application of the invention is to operate the primary element of the blade mechanism to change the dimension of the aperture during the imaging procedure. Such a solution can be advantageously used e.g. to improve radiation hygiene in dental panoramic imaging implemented using a narrow beam, where it will be possible to limit the area to be scanned e.g. individually for each patient so as to exclude the eyes in the mid-region of the imaging scan.

The invention claimed is:

1. A method for limiting a ray beam in connection with x-ray imaging equipment, in which at least one blade element of a blade mechanism (1) is moved by means of an actuator (3) so as to produce a ray beam of a desired form, wherein the method involves use of a blade mechanism (1) comprising a single primary blade element (4) and at least one secondary blade element (5, 20 etc.) in such manner that the single primary blade element (4) is moved independently of any other of said at least one secondary blade elements by means of the actuator (3), and said at least one secondary blade element (5, 20 etc.) arranged to limit the beam is moved in a manner such that it is driven by the movements of the primary element (4); and wherein the ray beam is limited by two blade elements, wherein at least one of said blade elements is a secondary blade element.

2. Method according to claim 1, wherein moving of said one secondary element (5, 20 etc.) is realized so at least in one moving direction of the primary element (4) the secondary blade element (5, 20 etc.) is driven by movements of the primary element (4) when said at least one secondary blade element is at an edge of a given operating range, said operating range consisting of at least one range of distances between the aforesaid blade elements, and remains stationary when being within said operating range regardless of the movements of the primary blade element (4).

3. The method according to claim 1, wherein the method comprises steps in which at least one secondary blade element (5, 20 etc.) is moved, if it is not in its desired position, to the desired position using he actuator (3) and the movements of the primary blade element (4) comprised in the blade mechanism (1), and in which the primary blade element (4), or another secondary blade element (5, 20 etc.) adjacent to the said at least one secondary blade element (5, 20) etc.) in question, is transferred to its desired position by using the same actuator (3).

4. The method according to claim 1, wherein a secondary blade element (5, 20 etc.) is moved by means of a synchronizing device (11, 11a) structurally connected to it and to at least one other blade element (4, 5, 20 etc), or a secondary blade element (5, 20 etc.) is pushed either by the primary blade element (4), by another secondary blade element (5, 20 etc.) adjacent to the said secondary element (5, 20 etc.) in question or by said synchronizing device (11, 11a).

5. The method according to claim 4, wherein the method comprises following steps:

the position of a given blade element (4, 5, 20 etc.) is identified and, if it is not its desired position, at least one of the blade elements (4, 5, 20 etc.) is moved in a desired initial position;

the primary blade element (4) is moved by means of the actuator (3) in a direction away from a secondary blade element (5, 20 etc.) whereby the secondary blade element (5, 20 etc.) in question—being drawn by the primary blade element (4) and the associated synchronizing device (11), and by the possible other blade elements (5, 20 etc.) and synchronizing devices (11a) comprised in the blade mechanism (1) between the primary blade element (4) and the secondary blade elements (5, 20 etc.) in question—is caused to move in the direction of the primary blade element (4) at a distance from it corresponding to a maximum limit distance of an operating range of the blade elements in question, and the movement is continued until the secondary blade element (5, 20 etc.) in question has moved to the desired position past a first edge of an aperture to be formed by the blade elements;

the direction of movement is changed and the primary blade element (4) is driven in the direction of the secondary blade element (5, 20 etc.) in question until a minimum limit distance of said operating range between them is reached;

the movement is continued and the secondary blade element (5, 20 etc.) is pushed into its desired positioned to form the aforesaid first edge of the aperture;

the direction of motion is changed again and the primary blade element (4) is driven—or the secondary blade element (5, 20 etc.) adjacent to the secondary blade element (20 etc.) in question in direction of the primary blade element (4) is drawn—to its desired position within the operating range, while the secondary blade element (5) in question remains stationary, to form the second edge of the aperture, or wherein the method comprises the steps:

the position of a given blade element (4, 5, 20 etc.) is identified and, if it is not in its desired position, at least one of the blade elements (4, 5, 20 etc.) is moved to a desired initial position;

the primary blade element (4) is moved by means of the actuator (3) in a direction towards a secondary blade element (5, 20 etc.), first until a minimum limit distance of an operating range between the blade elements in question is reached;

the movement is continued in the same direction thereby causing the secondary blade element (5, 20 etc.) in question to move in that direction at a distance from the primary blade element (4) corresponding to the said minimum limit value of said operating range between the blade elements in question;

the movement is continued until said secondary blade element (5, 20 etc.) in question has moved to a desired position to form a first edge of the aperture being formed between the secondary blade element (5, 20 etc.) in question and the primary blade element (4)—or between the said secondary blade element (5, 20 etc.) in question and another secondary blade element (5, 20 etc.) adjacent to it in the direction of the primary blade element (4);

the direction of motion is changed and the primary blade element (4) is driven—or the secondary blade element (5, 20 etc.) adjacent to said secondary blade element (20) in question in direction of the primary blade element (4) is drawn—to its desired position within the operating range, while the secondary blade element (5) in question remains stationary, to form the second edge of the aperture.

6. The method according to claim 5, wherein, when said second edge is formed, the primary blade element (4), or said other secondary blade element (5, 20 etc.) adjacent to the secondary blade element (20 etc.) in question, is driven past the second edge of the aperture to be formed between the blade elements, the direction of motion as changed and the primary blade element (4), or said other secondary blade element (5, 20 etc.) adjacent to the secondary blade element (20 etc.) in question, is driven to its desired position to form the second edge of the aforesaid aperture.

7. The method according to claim 1, wherein the aforesaid actuator (3) is used to move several secondary blade elements (5, 20 etc.) coupled together by means of synchronizing devices (11, 11*a*) to form element pairs, which may be fitted for different uses.

8. The method according to claim 1, wherein the method is applied in dental x-ray imaging, for purposes of limiting the x-ray beams used in panoramic and cephalometric imaging.

9. The method according to claim 1, wherein the ray beam is limited by means of two blade mechanism (1) arranged to limit the beam in directions perpendicular to each other.

10. The method according to claim 1, wherein at least one blade element (4, 5, 20 etc.) limiting the ray beam is moved during an imaging process in a different direction than an imaging direction of the ray beam.

11. The method according to claim 10, wherein said at least one blade element (4, 5, 20 etc.) limiting the ray beam is moved in a direction perpendicular to the imaging direction of the ray beam.

12. The method according to claim 10, wherein a synchronizing device (11) is provided between two blade elements (4, 5, 20 etc.), which allows at least one given fixed distance to be maintained between said blade elements, and that these two blade elements (4, 5, 20 etc.) are moved at said fixed distance from each other during the imaging process to implement a scanning motion of the ray beam at the object being imaged.

13. An apparatus for limiting a ray beam, said apparatus comprising:

at least one blade mechanism (1) for limiting a ray beam and an actuator (3) for moving at least one blade element (4, 5, 20 etc.) comprised in the blade mechanism (1), wherein the blade mechanism (1) comprises a single primary blade element (4) and at least one secondary blade element (5, 20 etc.), wherein said single primary blade element (4) is structured and arranged to be driven independently of said at least one secondary blade elements by means of the actuator(3), and wherein die apparatus comprises means arranged for moving said at least one secondary blade element (5, 20 etc.) in a manner such that said at least one secondary blade element is driven by the movements of said single primary blade element (4); and wherein the ray beam is limited by two blade elements, wherein at least one of said blade elements is a secondary blade element.

14. The apparatus according to claim 13, wherein said means for moving said at least one secondary blade element (5, 20 etc.) is arranged to operate as a function of distance between the blade elements in question so that, when the distance between the blade elements (4, 5, 20 etc.) in question corresponds to a limit value of at least one given operating range, determined by a range of distances between said blade elements, the aforesaid at least one secondary blade element (5, 20 etc.) moves in dependence upon the movements of the primary blade element (4) while the primary blade element (4) is being moved in at least one direction, and when the aforesaid distance is in the range between the limit values of much an operating range, the aforesaid at least one secondary blade element (5, 20 etc.) remains stationary regardless of the movements of the primary blade element (4).

15. The apparatus according to claim 13, wherein the aforesaid means for moving the elements (4, 3, 20 etc.) include at least one synchronizing device (11, 11*a*) connected to two blade elements (4, 5, 20 etc.), the coupling of said synchronizing device (11, 11a) to the blade elements (4, 5, 20 etc.) being arranged that, when the primary blade element (4) is moved in a direction away from a secondary blade element (5, 20 etc.) coupled to the said synchronizing device (11, 11a), this synchronizing device (11, 11a) will pull the secondary blade element (5, 20 etc.) in question when the distance between the primary blade element (4) and said secondary blade element (5, 20 etc) in question has reached or equals a maximum limit distance of an operating range associated with them, and when the primary blade element (4)is moved in a direction towards the secondary blade element (5, 20 etc.) in question, either the aforesaid primary blade element (4), another secondary blade element (5, 20) etc.) adjacent to the secondary blade element (5, 20 etc.) in question, or a synchronizing device (11, 11a) being connected to said secondary blade element (5, 20 etc.) in question and latched in a fixed position in relation to it, will push the secondary blade element (5, 20 etc.) in question when the distance between the said blade elements (4, 5, 20 etc.) in question reaches or equal a minimum limit distance of the said operating range, and/or in case the blade mechanism (1) comprises two or more secondary blade elements (5, 20 etc.), the blade elements (4, 5, 20 etc.) of the blade mechanism (1) are arranged adjacent to each other to form at least two pairs of adjacent blade elements (4, 5, 20 etc.), wherein said adjacent elements (4, 5, 20 etc.) are connected to each other by a synchronizing device (11, 11a).

16. The apparatus according to claim 15, wherein the synchronizing device (11, 11a) is a pin-like coupler connected by its first end to one blade element (4, 5, 20, etc.) and by its second end to an adjacent blade element (4, 5, 20 etc.) so that, when one blade element (4, 5, 20 etc.) is being moved in a direction away from an adjacent blade element (4, 5, 20 etc.), the synchronizing device (11, 11a, etc.) is able to pull the adjacent blade element (4, 5, 20 etc.) and, when one blade element (4, 5, 20 etc.) is being moved towards an adjacent blade element, the synchronizing device (11, 11a) will not cause the adjacent blade element (4, 5, 20 etc.) to move within at least one operation range between the said blade elements.

17. The apparatus according to claim 13, wherein the surface of a blade element (4, 5, 20 etc.) is provided with at least one slot-like groove (18).

18. The apparatus according to claim 17, wherein said at least one slot-like groove (18) is arranged to be able to incorporate a synchronizing device (11, 11a) arranged to be used to connect two blade elements (4, 5, 20, etc.).

19. The apparatus according to claim 18, wherein the lengths of the slot-like grooves (18) and synchronizing device (11, 11a) are so fitted in relation to each other that, when a blade element (4, 5, 20 etc.) is being moved, the synchronizing device (11, 11a, etc.) either moves the adjacent secondary blade element (5, 20 etc.), remains stationary or moves in the slot-like groove (18) without pulling or pushing said secondary blade element (5, 20 etc.).

20. The apparatus according to claim 13, wherein the apparatus forms a part of an equipment used in dental x-ray imaging, and/or it comprises a soft tissue filter attached to one of the blade elements (4, 5, 20 etc.).

21. The apparatus according to claim 13, further comprising a control system of the apparatus including means for driving the primary blade element (4) during an imaging process.

22. The apparatus according to claim 13, wherein the apparatus comprises two blade mechanisms (1) arranged to limit the beam in perpendicular direction relative to each other.

23. The apparatus according to claim 21, wherein the apparatus comprises a blade mechanism (1) that has been arranged to limit an aperture between two elements (4, 5, 20 etc.) in the vertical direction so that the primary blade element (4) of it is caused to limit the upper edge of the beam being limited, and that the control system of the apparatus comprises means for driving the primary blade element (4) during said imaging process.

24. The apparatus according to claim 13, wherein at least one fixed distance has been arranged between two blade elements (4, 5, 20) etc.) that the width of a beam limited between said two blade elements in this position is applicable for use in a given scanning imaging process.

25. The apparatus according to claim 24, wherein said fixed distance corresponds to a maximum limit value of an operating range between the primary blade element (4) and an adjacent secondary blade element (5).

26. The apparatus according to claim 13, wherein synchronizing devices (11, 11a) are arranged between the blade elements to connect two blade elements (4, 5, 20, etc.), said synchronizing devices having different lengths.

27. The apparatus according to claim 13, wherein the apparatus include at least one synchronizing device (11, 11a) structurally connected to at least two blade elements (4, 5, 20 etc.), said synchronizing device (11, 11a) having means to lock it in at least one fixed position in relation to at least one blade element (4, 5, 20 etc.).

28. The apparatus according to claim 13, wherein the primary blade element (4) of the blade construction (1) is at unitary U-shaped element with two blades at a distance from each other, and wherein at least one secondary blade element (5, 20 etc.) is arranged to be narrower than said distance between said two blades.

\* \* \* \* \*